United States Patent [19]

Harvey et al.

[11] Patent Number: 4,756,902
[45] Date of Patent: Jul. 12, 1988

[54] CAPSULE SEALING PROCESS AND PRODUCT

[75] Inventors: Larry L. Harvey, Lebanon; Bakul T. Doshi, East Petersberg; Edward W. Sunbery, Lancaster, all of Pa.

[73] Assignee: Warner-Lambert Company, Morris Plains, N.J.

[21] Appl. No.: 891,006

[22] Filed: Jul. 25, 1986

Related U.S. Application Data

[63] Continuation-in-part of Ser. No. 869,748, Jun. 2, 1986, abandoned.

[51] Int. Cl.$^4$ .................... B65B 51/02; B65B 51/20; A61K 9/48
[52] U.S. Cl. ..................... 424/454; 53/478; 53/485; 53/900; 206/828
[58] Field of Search ............... 53/900, 471, 477, 478, 53/467, 454; 424/37; 206/438, 828; 156/294, 308.4, 308.6

[56] References Cited

U.S. PATENT DOCUMENTS

| | | | |
|---|---|---|---|
| 2,314,527 | 3/1943 | Taylor | 53/900 X |
| 2,936,493 | 5/1960 | Scherer | 53/900 X |
| 3,073,087 | 1/1963 | Sandhage et al. | 53/900 X |
| 3,078,629 | 2/1963 | Besemer et al. | 53/900 X |
| 3,162,000 | 12/1964 | Kraven | 53/900 X |
| 3,200,556 | 8/1965 | Ackley | 53/900 X |
| 3,927,195 | 12/1975 | Messora | 53/900 X |
| 4,415,387 | 11/1983 | Newman | 156/294 X |
| 4,478,658 | 10/1984 | Wittwer | 156/294 X |
| 4,584,817 | 4/1986 | Yamamoto et al. | 53/900 X |
| 4,656,066 | 4/1987 | Wittwer . | |

*Primary Examiner*—Horace M. Culver
*Attorney, Agent, or Firm*—Howard Olevsky; Stephen Raines

[57] ABSTRACT

A method for sealing capsules which comprises contacting the cap and body juncture with a sealing solution of alcohol and water maintained between about 40° C. to the boiling point of the fluid. A secondary gelatin band seal is also contemplated in one aspect of the invention, as well as a capsule having both seals.

13 Claims, No Drawings

CAPSULE SEALING PROCESS AND PRODUCT

CROSS REFERENCE TO RELATED APPLICATION

This application is a continuation-in-part of U.S. Ser. No. 869,748 filed June 2, 1986 by the same inventors and bearing the same title and now abandoned.

FIELD OF THE INVENTION

This invention relates to methods for sealing capsules and particularly methods for sealing capsules which provide a tamper resistant seal between the capsule parts.

BACKGROUND OF THE INVENTION

Hard shelled gelatin capsules have a disadvantage in that the cap and body parts can be opened and rejoined without the disruption becoming externally visible.

Capsules which are telescopically joined have only a partial overlap of the cap side wall with the body side wall. This allows for gripping and withdrawal of the body part thereby making separation relatively easy.

One of the ways utilized to seal the capsule components to inhibit this easy separation is by banding. This process uses a gelatin solution which is rolled on the capsule at the juncture between the body and cap lip to form a band. While banding is successful against attempts at physical separation of the cap and body of the capsule, it is susceptible to disruption in the same way that the unmodified shell capsule components are.

Various attempts have been made to seal the body and head of the capsule directly to each other by means of a so-called "sealing fluid."

Prior art for capsule sealing is contained in the following patents:

U.S. Pat. No. 3,071,513, issued Jan. 1, 1963 to H. R. DeBoer et al. which discloses a sealing fluid comprising a dispersion of an air-drying hydrophilic, film-forming polymer in an organic solvent. The application of the sealing fluid was by dipping the capsules.

U.S. Pat. No. 3,159,546, issued Dec. 1, 1964 to J. R. Kane, discloses a liquid sealant consisting of three components containing by weight from about 1 to 4½ parts, preferably 3 to 4½ parts, of acetone; from about 1½ to 2 parts, and preferably 1¼ to 2 parts, of water; and from about ¾ to 2¼ parts, and preferably about ¾ of a part, of ethyl acetate.

U.S. Pat. No. 2,924,920, issued Feb. 16, 1960 to Elly T. Margolis, discloses a three components mixture containing a polyhydric alcohol, an alcohol and water. This composition is used to seal capsules by a swelling technique. The process is designed to avoid solvent penetrating the overlap between capsule body and cap.

French Pat. No. 2,118,883, issued June 6, 1975 to Green Cross Corporation, discloses the use of alcohol and water in an enteric coating process.

U.S. Pat. No. 4,539,060, issued to Fritz Wittwer and Ivan Tomka on Sept. 3, 1985 describes sealing by contacting the capsules with a stream of sealing fluid which is then positioned between the overlap of the cap and body parts by capillary action. Excess sealing fluid is then drained of excess fluid and the capsule parts with the fluid in place is subjected to thermal energy. Several sealing fluids are suggested in this patent including aqueous solutions of salts, cations and ions, water and polymer solutions or emulsions.

European Patent Application Ser. No. 152,517 discloses the use of thermal energy in conjunction with a mixture of alcohol and water to provide a seal between the cap and capsule body wherein as with the Wittwer et al. patent, the fluid is positioned by capillary forces between the cap and the capsule body and subsequently heated in situ.

The tamper-resistant sealing prior art, therefore, is generally of two types. That which requires the addition of an added element which seals the overlap between the capsule cap and body and those which by the choice of appropriate solvents unite the cap and body. However, it has been found that, when using a sealing agent within the overlap of the cap and body portions without the application of heat, the seal is generally insufficient to maintain a liquid medicament in the capsule. Also, when heat is applied, numerous localized distortions of the capsule wall occur, so that further handling is extremely difficult.

SUMMARY OF THE INVENTION

According to this invention, distortion in liquid sealed capsules resulting from the application of heat can be avoided by sealing with sealing fluid maintained between about 40° C. and about 100° C. for a time sufficient to provide formation of a unitary capsule wall.

DETAILED DESCRIPTION OF THE INVENTION

It has been found that by locally applying only small amounts of sealing fluid maintained between about 40° C. and 100° C. in the area of the seal, an excellent seal without distortion of the capsule walls is produced.

The sealing fluid is essentially evenly distributed between the overlapping sections of the cap and body parts of the gelatin capsule by capillary effect. This effect is achieved when the contact angle between a drop of the sealing fluid and the gelatin film is small.

The mechanism of the capillary effect is described by Walter J. Moore in Physical Chemistry, 4th Edition, pages 479–481, Longman Edition London, England (1978) as follows: "Whether a liquid rises in a glass capillary depends on the relative magnitude of the forces of cohesion between the liquid molecules themselves and the forces of adhesion between the liquid and the walls of the tube. These forces determine the contact angle which the liquid makes with the tube walls. If this angle is less than 90° C., the liquid is said to wet the surface and a concave meniscus is formed."

The wettability of gelatin films is measured as "adhesional wetting" where a liquid not originally in contact with a substrate, makes contact with that substrate and adheres to it.

The sealing fluid of this invention is basically a mixture of alcohol and water. The alcohols that may be employed in this invention are preferably aliphatic monohydric alcohols of from 1 to 4 carbon atoms which may also be substituted by one alkoxy group having one or two carbon atoms, and mixtures thereof. Additionally, surfactants may be added in small amounts to enhance the capillary action of the sealing fluid but this is not necessary.

Of prime importance is the miscibility of the alcohols with water and their ease of removal after contact with the capsules. In view of this, the preferred alcohols are isopropanol, 2-propanol, ethanol, methanol and mixtures thereof. The most preferred is ethanol. The alcohols used in the present invention are employed in combination with water. The relative ratios of the alcohol to water should be in ranges so that all the components are completely miscible in each other.

The alcohol primarily lowers the surface tension of the water while the water lowers the melting point of the gelatin and promotes the sealing. The molten gelatin surfaces of the overlapping sections of capsule cap and body parts yield complete seal, without giving any distortions. (Besides the melting point depression effect some denaturation of the gelatin may occur.)

The proportion of alcohol and water are based on a ratio of alcohol to total solution on a volume/volume base. The percent alcohol which may be one or a mixture of the alcohols of the invention, is from about 20 to about 50% preferably from 25–35% while that of water is from about 50% to about 80%, especially 65–80%.

The frangibility of the sealed capsule is apparently directly related to the amount of alcohol present in the sealing solution. While frangible capsules are more difficult to handle, they also more readily reveal attempts at tampering and therefore a balance is desirable between these opposite considerations. It should be noted that frangibility is more readily tolerated in smaller capsules. Overall capsule size, therefore, is another consideration in determining proper alcohol water ratios.

Time needed for sealing while ranging from 1 second to 5 minutes varies inversely with the percent of alcohol used, although sealing is impossible at temperatures below 40° C. It has also been found that capsule distortion is directly related to temperature and contact time of the sealing solution. Therefore, lower temperatures higher levels of alcohol and shorter contact times with the operative ranges are currently preferred. It should be noted that precise times are extremely difficult to define, because sealing is not an instantaneous process but, rather a continuous one and as will be seen from the description of the preferred process of this invention, the time of exposure to a heated fluid, is an approximation.

The preferred process of this invention involves the use of a banding machine to provide the liquid sealing, and, in a particularly preferred aspect, a gelatin band is positioned over the liquid sealed area as a second seal.

One of gelatin capsule banding machines in use currently, employs a turntable with radially-aligned, capsule-engaging slots. The capsules with their long axis radially aligned in the slots, advance to a work station, where they are contacted with a print wheel positioned below the turntable, which has been coated with gelatin from a reservoir through which the print wheel rotates.

The process of this invention utilizes the approach and apparatus described above relative to gelatin banding. Instead of gelatin in the reservoir, sealing fluid maintained between about 40° C. to 100° C., although it is preferred to keep the temperature below about 60° C. to minimize the impact of thermal energy on the capsule. The print wheel provides sufficient fluid to accomplish liquid sealing without adding large quantities of fluid to the capsule surface which must ultimately be removed. While other methods of applying small amounts of precisely located fluid, such as by use of nozzles, are contemplated within the scope of this invention, the print wheel reservoir system is preferred because of its simplicity, ease of use, ability to precisely position small amounts of sealing fluid and its compatibility with banding equipment. Print wheels between 1 and 3 mm in printing surface thickness, i.e., axial thickness have proven particularly useful.

When a subsequent gelatin banding step is added, the quality of the band is dependent on the dryness of the capsule surface, and application of precisely directed small amounts of fluid are especially critical when the gelatin band is employed after the liquid seal is completed.

The liquid sealing process of this invention has several advantages when compared to the prior art liquid sealing steps and these advantages result regardless of the addition of a subsequent banding step.

First, sealing occurs at the time of contact with heated fluid, thus eliminating the need for a separate heating step.

Second, heat is applied only at the area of sealing due to the use of elevated temperature sealing fluid at the only source of thermal energy. This heating step eliminates the capsule wall distortion resulting from localized thermal energy absorption which occur when heat is applied external to the sealing joint. The external application of heat is a requirement for prior art liquid sealing processes. Difficulties inherent in capsule pigment heat absorption are also eliminated by this technique.

Third, this sealing step is simple, adaptable to currently available apparatus and is compatible with a subsequent gelatin banding.

Further, since sealing occurs coincidentally with fluid positioning in the joint between capsule cap and body, and the sealing is conducted at environmental temperatures below that of the sealing fluid, the thermal energy applied to the joint to accomplish the sealing, rapidly dissipates. This dissipation makes heat related distortion virtually impossible. It should be noted that this energy dissipation which starts to occur almost instantaneously, makes it virtually impossible to put precise time limits on this process step.

The nature of the fluid addition according to this invention also makes it difficult to precisely define the fluid temperature during sealing and "maintaining the temperature during sealing" as used herein refers to the fluid temperature at the time it contacts the cap and body overlap.

As mentioned previously, a subsequent banding step is particularly preferred and its success is dependent on the dryness of the capsule in the area where the gelatin band is applied. This area which is, at the time of banding, a part of a continuous capsule surface, is where the previous liquid sealing occurred. While virtually no fluid after sealing with a print wheel applicator is present on the capsule, a positive drying step is preferred such as passing the capsules through a low humidity forced air tunnel when banding is used.

If subsequent banding is not performed, the capsule surface still must be dry but this can occur by allowing the small amount of surface liquid to evaporate.

When banding is utilized, it is currently preferred to alter the turntable by utilizing two separate work stations, each with print wheels, reservoir and capsule spinning means which have been separated by a drying tunnel such as the one previously described. Ultimately the speed and/or shape of the turntable may be altered to accommodate high volume capsule sealing.

While the liquid seal of this invention provides a unitary sealed capsule by itself, the secondary seal offers several distinct advantages when used in conjunction with the liquid seal. First it provides an added measure of safety in the unlikely event that microscopic defects or distortions occur in the sealing area. Second, when used with the liquid seal process of this invention it prevents the appearance of pigment bleeding of the cap and body colors. Third, it also serves as an immediate visual indicator of a tampering attempt directed at the seal joint.

Fourth, because the process for the liquid sealing step according to this invention is simple and sequentially compatible, i.e., the banding apparatus need be only slightly modified, there is little added process complexity.

Optionally, after banding is completed, thermal energy may be employed to speed the band formation although it is not required. If thermal energy is employed low levels for short periods, ranging no more than several seconds are preferred.

Sealing by the present invention can be used for telescopically joined gelatin capsules which are empty or have powders, pastes, tablets or granules, microcapsules, etc., solids in liquids, liquids in solids, or liquids for any combination of the above. The liquid sealing described above is a preferred process for sealing liquid components since it provides a continuous capsule surface which prevents leakage.

What is claimed is:

1. A method for sealing a gelatin capsule having a body and a cap with the inner circumference of said cap at its edge being greater than the outer circumference of the capsule body, said method comprising:
   (a) aligning said cap edge to surround said body edge;
   (b) contacting the juncture of the cap and body edge with a sealing fluid containing an alcohol-water solution maintained at about 40° C. and about 100° C. to form a liquid seal and continuous surfaced capsule; and
   (c) applying a gelatin band to gird the capsule in the area of the liquid seal.

2. The method of claim 1 wherein the sealing fluid comprises from about 50% to 80% water and about 50 to about 20% of at least one member selected from the group of monohydric alcohol having from 1 to 4 carbon atoms, a monoalkoxy-substituted aliphatic monohydroxy alcohol containing 1 to 4 carbon atoms with said alkoxy group containing not greater than 2 carbon atoms said percentages on a volume/volume basis.

3. The method of claim 1 wherein the alcohol is ethanol.

4. The method of claim 1 wherein the capsule surface is dry prior to the addition of the gelatin band.

5. The capsule made according to the method of claim 1.

6. The method of claim 1 wherein the sealing fluid is maintained at a temperature not greater than about 60° C.

7. A method for liquid sealing of a gelatin capsule having a body and a cap with the inner circumference of said cap as its edge being greater than the outer circumference of the capsule body said method comprising:
   (a) aligning said cap edge to surround said body edge;
   (b) contacting the juncture of the cap and body edge with an aqueous sealing fluid solution containing from 20 to 50 parts by weight of ethanol on a volume/volume basis while maintaining said fluid between about 40° C. and about 60° C.; and
   (c) applying a gelatin band to gird the capsule on a dry surface in the area of the liquid seal.

8. The method of claims 1 or 7 wherein the capsule body and cap are simultaneously spun as the sealing fluid is applied.

9. The method of claims 1 or 7 wherein a print wheel is used to apply the sealing fluid.

10. The method of claims 1 or 7 wherein excess sealing fluid from liquid sealing is removed from the capsule surface by forced air drying.

11. The method of claims 1 or 7 wherein a print wheel with an axial thickness of 1 to 3 mm is used to apply the sealing fluid.

12. The method of claims 1 or 7 wherein thermal energy is applied to the capsule after gelatin banding is completed, the thermal energy applied in the area of said band.

13. The method of claims 1 or 7 wherein the ethanol is present at a level of between 25 and 35%.

* * * * *